(12) United States Patent
Håkansson et al.

(10) Patent No.: US 6,217,557 B1
(45) Date of Patent: Apr. 17, 2001

(54) DEVICE FOR INJECTING A SUBSTANCE INTO A BODY, ESPECIALLY HUMAN OR ANIMAL

(75) Inventors: Håkan Håkansson, Lund; Jan-Erik Olsson, Linköping; Jonas Wallinder, Vikingstad, all of (SE)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/180,935
(22) PCT Filed: Mar. 21, 1997
(86) PCT No.: PCT/SE97/00492
  § 371 Date: Nov. 16, 1998
  § 102(e) Date: Nov. 16, 1998
(87) PCT Pub. No.: WO97/44079
  PCT Pub. Date: Nov. 27, 1997

(30) Foreign Application Priority Data

May 23, 1996  (SE) .................................................. 9601974

(51) Int. Cl.⁷ .................................................. A61M 5/178
(52) U.S. Cl. ...................................... 604/167.06; 604/158
(58) Field of Search ................................. 604/158, 166, 604/167, 169, 264, 268, 251

(56) References Cited

U.S. PATENT DOCUMENTS 5,116,344    5/1992  Sundqvist .
5,817,072  * 10/1998  Lampropoulos et al. ........... 604/264

FOREIGN PATENT DOCUMENTS

3539243 C3  *  5/1987  (DE) .

* cited by examiner

Primary Examiner—Sharon Kennedy
Assistant Examiner—Catherine Serke
(74) Attorney, Agent, or Firm—Burns, Doane, Swecker & Mathis L.L.P.

(57) ABSTRACT

A device for injecting a substance into a body, especially human or animal, comprising a cannula or needle member (4–6) and a dosing device (8) for supplying a determined amount of substance (10) to a target area (1), the dosing device having an attachment (7) for the cannula or needle member. The invention is characterised in that the cannula or needle member (4–6) comprises a tube (4) and a catheter (6) which is displaceable in the tube, the outer diameter of the catheter being smaller than the inner diameter of the tube, thereby forming a gap between the catheter (5) and the tube (4), essentially over the entire length of the tube (4), in that the proximal portion of the catheter is attached to the dosing device (8), and in that the distal portion (9) of the catheter, in connection with said injection, is arranged adjacent to the distal end (12) of the tube (4) and forms a fluid-tight seal therewith.

20 Claims, 4 Drawing Sheets

DEVICE FOR INJECTING A SUBSTANCE INTO A BODY, ESPECIALLY HUMAN OR ANIMAL

TECHNICAL FIELD

The present invention relates to a device for injecting a substance into a body, especially human or animal, comprising a cannula or needle member and a dosing device for delivering a determined amount of substance to a target area, the dosing device having an attachment for the cannula or needle member. The invention also concerns a method for injecting the substance, comprising the steps of defining the target area, inserting a cannula or needle member in the body so as to position the tip portion of the member at the target area, supplying a determined amount of substance to the target area, and removing the cannula or needle member.

BACKGROUND OF THE INVENTION

In the medico-technical field, several methods of introducing liquid, with or without solid particles, into the body are already available. Most of these methods are based on the use of a needle or catheter in combination with some pumping device such as syringes or infusion pumps. In most applications, the volume of infused or injected liquid, liquid mixture or suspension is also relatively great relative to the dimensions or inner volume of the insertion system, which results in the influence of the system on the final position of the inserted fluid volume in the body being affected only marginally when withdrawing the insertion system. In most applications, the position of the deposition is also not decisive of the clinical efficiency of the infused substance.

In recent years, the requirements for accuracy of the deposition have increased dramatically in the field of, among other things, tissue implants. An example of fields where the accuracy of the deposition is highly decisive of the clinical result is the implantation of cells for treating Parkinson's disease. Cells which preferably are extracted from a foetus are suspended in a physiological solution, which is inserted to the desired position in the brain. The amount of suspended cells is in the order of 10 μl, which corresponds to the volume in a 10 mm length of the catheter by which the substance is introduced. Problems arise when the catheter system is being withdrawn, since a vacuum is generated which sucks back a great part of the infused amount to a non-desired position, resulting in the fact that the implanted cells cannot develop and contribute to a positive clinical effect.

SUMMARY OF THE INVENTION

The object of the present invention is to satisfy the requirements described above, while eliminating the drawbacks of prior-art systems.

A further object is to provide a method and a device, by which a substance which in medical contexts is suitable, can be injected with accuracy and in its entirety into a restricted and well-defined target area in a patient's body.

One more object of the invention is to permit the use of a flexible catheter for a simplified injection process.

According to the invention, these objects are achieved by a device according to the introductory part, which is characterised in that the cannula or needle member comprises a tube and a catheter displaceable in said tube, the outer diameter of the catheter being smaller than the inner diameter of the tube, thereby forming a gap between the catheter and the tube, essentially over the entire length of the tube, in that the proximal portion of the catheter is attached to the dosing device, and in that the distal portion of the catheter is, in connection with said injection, arranged adjacent to the distal end of the tube and forms a fluid-tight seal therewith.

A method for manipulating the device as described above is characterised in that the cannula or needle member is inserted into the body, the tip portion thereof being sealed by means of a sealing member which forms a fluid-tight seal with a surrounding tube of the cannula or needle member, in that the substance is injected into the target area by means of a catheter, which is surrounded by said tube and whose distal portion has, on the occasion of injection, been brought close to the distal portion of the tube, in that the catheter is then withdrawn from the body, thereby allowing air or gas at essentially atmospheric pressure to enter the space in the tube between the target area and the distal portion of the catheter, and in that finally the tube is withdrawn from the body and the insertion opening for the cannula or needle member is closed.

BRIEF DESCRIPTION OF THE FIGURES

Preferred embodiments of the invention will now be described for the purpose of exemplification, reference being made to the accompanying drawings, in which.

DETAILED DESCRIPTION OF THE INVENTION

Figure 1:
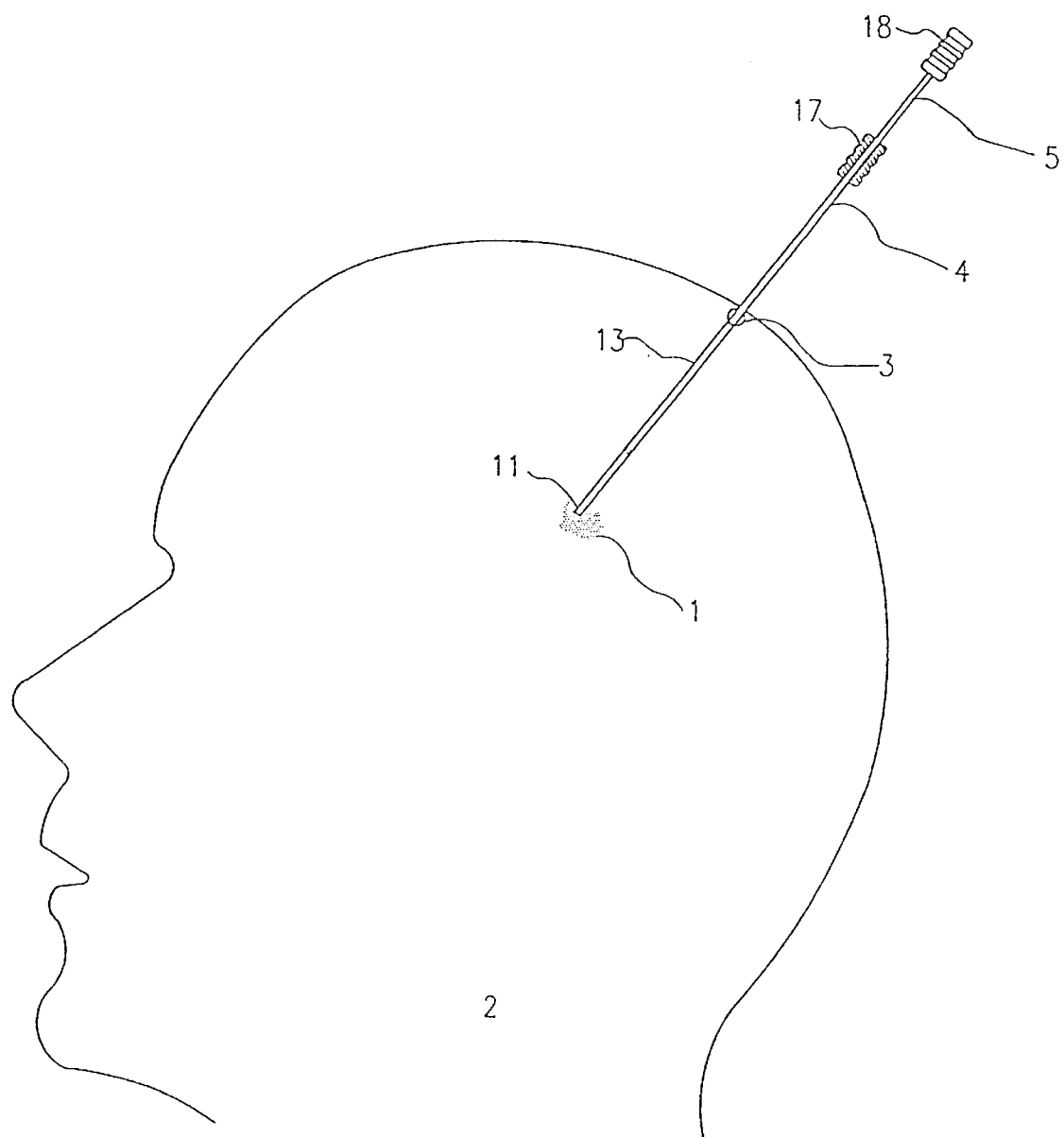
FIG. 1 illustrates an embodiment of the inventive device inserted to the target area, in a patient's brain, but before injecting a medical substance.
Figure 2:
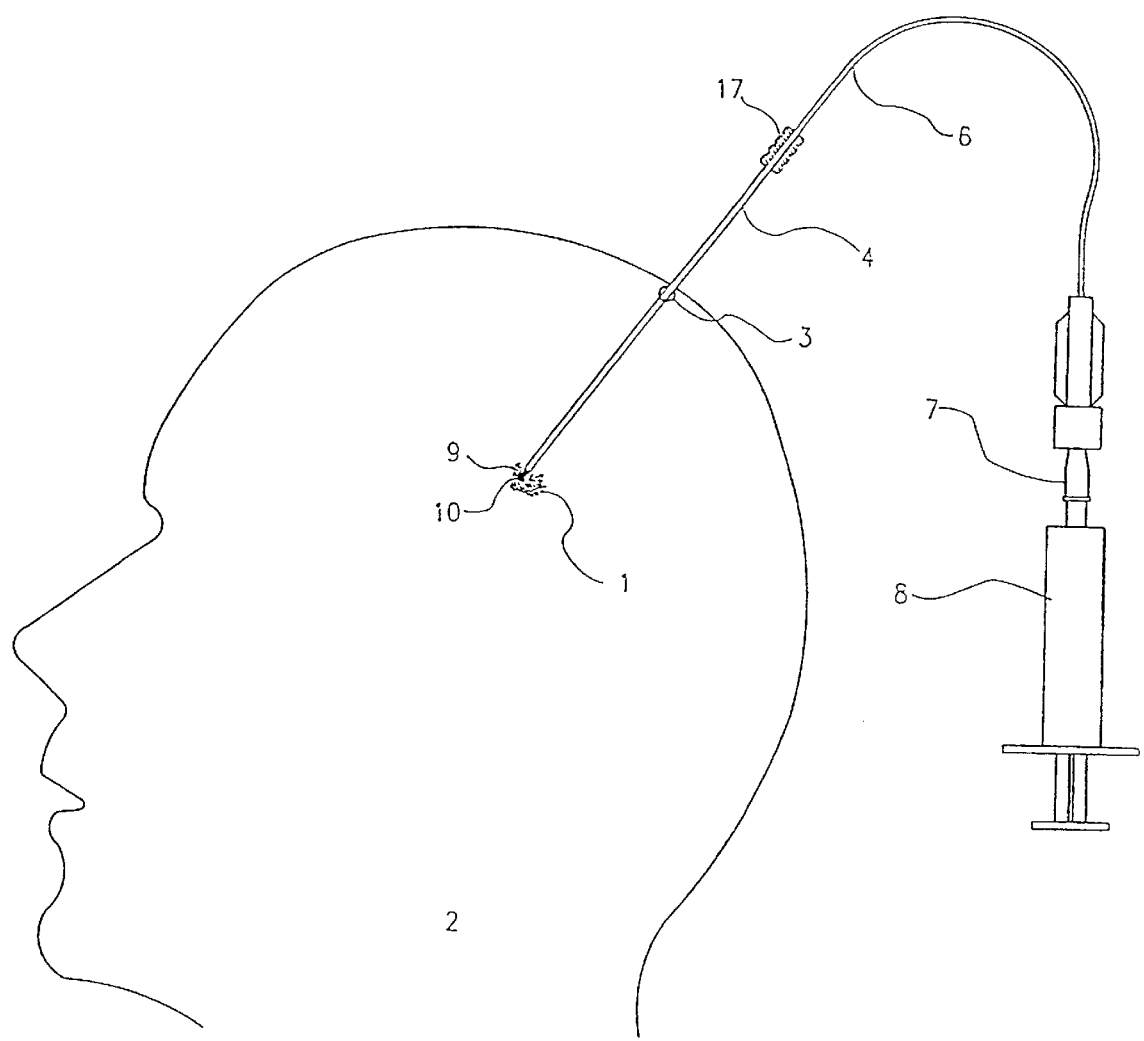
FIG. 2 is the same view as in FIG. 1, illustrating a dosing device with a catheter connected, whose distal end is positioned adjacent to the target area, after injecting the substance.
Figure 3:
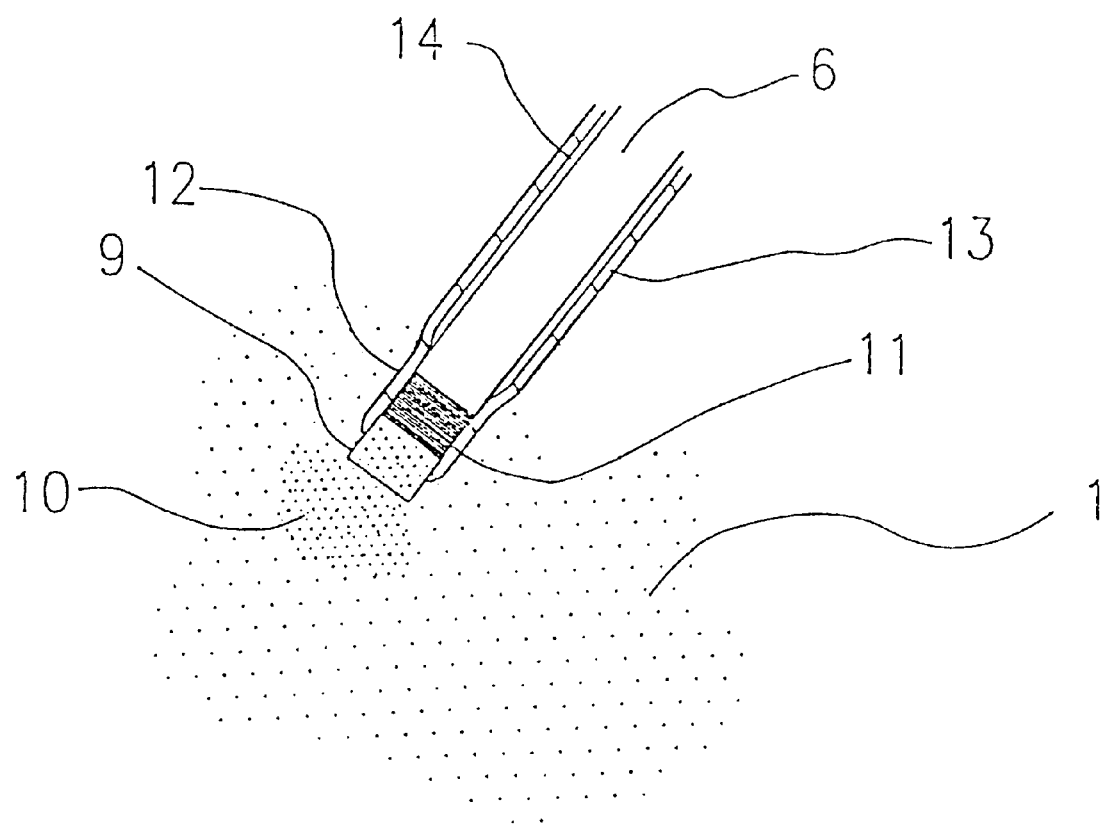
FIG. 3 illustrates on a larger scale the tip portion of the cannula or needle member in the target area during injection.

With reference first to FIGS. 1–3, the injection or infusion device according to the invention comprises an outer tube 4 of a suitable surgical material. Preferably, the tube is rigid and made of stainless steel. The distal tube portion 12, which is adapted to be positioned adjacent to a target area 1 in the patient's body, has in this embodiment a smaller diameter and a considerably shorter length than the proximal tube portion 13, which projects from the patient's body. In the preferred embodiment, the length of the entire tube is about 200 mm and the length of the area having a smaller diameter is about 1 mm. The outer diameter of the tube is about 2 mm and its inner diameter is about 1.6 mm except in the area of a smaller diameter, where the inner diameter is about 1.3 mm. In FIG. 3, the difference in diameter is clearly shown, and the reason for this difference will be explained below.

Thus, the tube 4 is adapted to be inserted into a patient's (a human or an animal) body and in order to facilitate this, the proximal portion of the tube can be fitted with a finger grip portion 17, as illustrated in FIG. 1. This figure shows the tube 4 inserted in the patient's skull 2 for injecting a cell suspension into a target area 1 in the brain as above, but it is to be understood that the inventive device can just as well be used to inject an optional substance which is suitable in medical contexts, such as a pharmaceutical preparation, cytotoxin, contrast fluid etc, into a patient's internal organs, spinal marrow, tissue etc. The main inventive object is injection of a small amount of substance into a well-defined target area.

Reference is again made to FIG. 1, illustrating that the tip portion or distal portion 12 of the tube 4 has been positioned at the target area 1. When inserting the tube 4 into the skull 2, a mandrin 5 is stationarily and releasably arranged in the tube. The mandrin is formed as a cylindrical rod of uniform thickness, preferably of the same material as, but longer than the tube 4 and also having a finger grip portion 18 at its proximal portion. The outer diameter of the mandrin 5 is the same as the inner diameter of the distal tube portion 12, in this case about 1.3 mm. This results in a seal against the inner side of the tube in the distal portion 12 thereof against penetration of cerebral substance, blood, tissue material and the like into the tube 4 when inserting it into the skull 2. Moreover, an essentially concentric gap 14 is formed between the mandrin 5 and the tube portion having a greater diameter 13, which gap is open to the atmosphere. If desired, the gap can alternatively be connected to a gas source (not shown) having a pressure slightly exceeding atmospheric pressure for reasons that will be explained below. If necessary, an additional sealing member, e.g. an O-ring, can be arranged in prior-art manner on the distal end of the mandrin (not shown).

When the tube 4 has been positioned, the mandrin 5 is withdrawn from the tube, and initially a vacuum arises in the distal portion 12 of the tube, but owing to the small length of this portion and owing to the gap 14 which serves as a pressure-equalising member, the vacuum is eliminated almost immediately, and therefore essentially no matter will be sucked into the tube 4.

The inventive device also comprises a catheter 6, preferably in the form of a plastic tube, whose outer diameter is the same as that of the mandrin, i.e. in this case about 1.3 mm, so as to obtain the same sealing effect as with the mandrin. Its inner diameter (lumen) is in this example about 0.9 mm and its length in the order of 300–400 mm. The proximal portion of the catheter is, for instance by means of a so-called Luer connection 7, attached to a dosing device/injection device 8, which in FIG. 2 is schematically illustrated as a syringe.

After removing the mandrin 5 from the tube 4, the catheter 6 is inserted therein and is guided thereby. The air or gas in the tube flows out through the above-mentioned gap 14, which is now delimited by the inner diameter of the tube 4 and the outer diameter of the catheter (which is the same as that of the mandrin). The catheter 6 is preferably inserted so far that its tip is positioned immediately outside the tip of the tube, as shown in FIG. 3. If necessary, additional sealing means, for instance ridges 11 as indicated in FIG. 3, can be arranged on the distal portion of the catheter. When the catheter 6 has been positioned, a determined amount of substance 10, e.g. a cell suspension, is infused or injected into the target area 1 by means of the dosing device/injection device 8. When the infusion has been carried out, the catheter 6 is withdrawn from the tube 4, whereby pressure equalisation occurs in the same manner as described above in connection with the withdrawal of the mandrin 5. Then the tube 4 communicating with the atmosphere or a gas source as stated above is withdrawn, which means that there will be no negative pressure.

In FIG. 3, reference numeral 11 indicates a number of parallel ribs or ridges which are circumferentially oriented. In another embodiment, reference numeral 11 indicates, however, an X-ray marker for identifying the position of the catheter end in the body.

Figure 4:
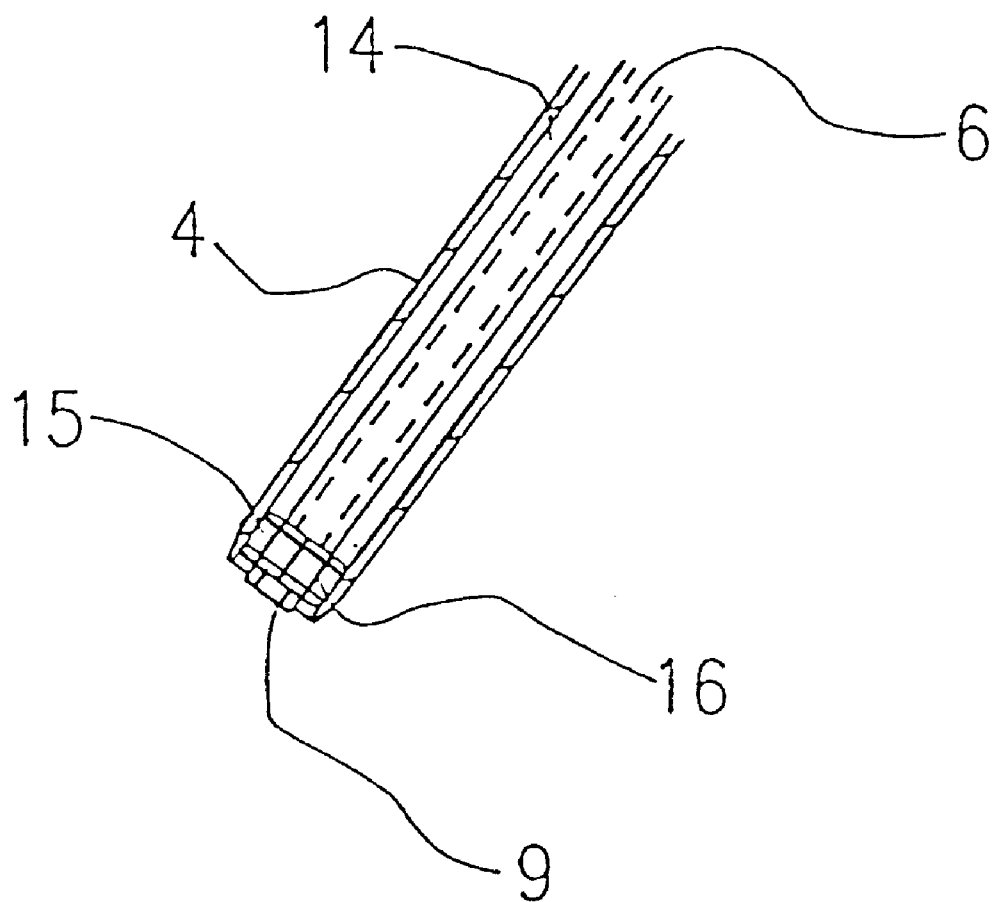
FIG. 4 is the same view as in FIG. 3, illustrating an alternative embodiment of the device according to the invention.

FIG. 4 illustrates an alternative embodiment of the device according to the invention. What essentially distinguishes this embodiment from the one previously presented is that it comprises no mandrin. The catheter 6 is in place even when inserting the cannula or needle member, i.e. in this case, the tube 4. The tube can also in this case be of the design presented above—a short distal portion having a small inner diameter and a long proximal portion having a greater inner diameter—but a tube having a constant inner diameter is preferred. At the distal portion of the catheter 6, a piston-shaped member 15 is arranged in a fixed or integrated manner on the outer surface of the catheter. The piston-shaped member 15 is slidingly engaged with the inner surface of the tube 4 and serves as a sealing member for the gap 14 between the tube and the catheter. In its cylindrical peripheral surface, the member 15 has a plurality of essentially axially oriented grooves or channels 16 of such small dimensions that it does not allow the passing of substance or fluid, but allows the passing of air or gas, thereby preventing any matter from penetrating into the gap 14 when inserting the cannula or needle member, but permitting pressure equalisation when the catheter after the injection is being withdrawn from the tube 4. Penetration of any matter into the lumen of the catheter during said insertion is counteracted by the fluid column therein. The rigidity of the plastic material of the catheter 6 is such as to allow the counterpressure during said insertion to be absorbed by the catheter, and its lateral outward bend, if any, is restricted by the surrounding tube 4.

The method for injecting or infusing a substance into a patient by the inventive device has been described above in broad outline, but a brief description may be justified.

First the size and position of the target area in the body are defined and then the cannula or needle member is inserted into the body so as to position its tip proportion at the target area 1.

In the Example illustrated in FIGS. 1 and 2, this takes place in such a manner that a hole 3 is made in the cranial bone and the tube 4 with the retracted mandrin 5 or catheter 6 and the piston member 15 are positioned in the relevant area in the brain. This is carried out suitably by means of a device as described in ELEKTA INSTRUMENT AB's European Patent Application 312,568 (U.S. Pat. No. 5,116,344) or by means of the above-mentioned marker 11. In the embodiment shown in FIG. 2, the catheter is filled with a solution, whereupon a calculated dose of cell suspension 10 is sucked into the distal portion of the catheter. When the mandrin has been withdrawn from the tube 4, the charged catheter 6 in the tube 4 is inserted in position, cf. FIG. 3, for instance by means of a marking or scale on the outer surface of the catheter on the same level as the proximal end of the tube, cf. FIG. 2. The cell suspension 10 is then infused by means of the injection device 8, and the catheter 6 is removed from the body (tube) during pressure equalisation as described above. Then the tube 4 is removed and the insertion opening 3 is sealed.

In the embodiment shown in FIG. 4, the substance (cell suspension) is already in place in the distal portion of the catheter when the tube 4 along with the catheter 6 is inserted in the patient.

The invention is not restricted to that described above or shown in the drawings, but can be modified within the scope of the appended claims.

What is claimed is:

1. A device for injecting a substance into a body, comprising:

a cannula and a dosing device for delivering a determined amount of substance to a target area, the dosing device having an attachment for the cannula, wherein the cannula comprises a tube and a catheter slidably disposed in said tube, the outer diameter of the catheter being smaller than the inner diameter of the tube, thereby forming a gap between the catheter and the tube, essentially over the entire length of the tube, wherein the tube includes a terminal end for positioning proximal to the target area, said tube being defined by a distal tube portion including said tube terminal end and a second opposing end, and a proximal tube portion extending from said second end of said distal tube portion, said distal tube portion having a first diameter and said proximal tube portion having a second diameter, said first diameter being smaller than said second diameter, and wherein the catheter includes a terminal end, said catheter having a distal portion, including said catheter terminal end, and a proximal portion attached to the dosing device, the terminal end of the catheter being arranged for injection such that said catheter terminal end is immediately adjacent to the second opposing end of said distal tube portion and forms a fluid-tight seal therewith.

2. The device as claimed in claim 1, wherein the gap is open to the atmosphere or connected to a gas source having a low positive pressure.

3. The device as claimed in claim 1, wherein a sealing member is arranged on the distal portion of the catheter in sealing engagement with the interior of the tube.

4. The device as claimed in claim 1, wherein the tube has a short distal portion having a smaller inner diameter than a remainder of the tube, and in that said inner diameter is essentially as large as the outer diameter of the catheter.

5. The device as claimed in claim 1, wherein the cannula also comprises a mandrin displaceable in the tube and being in the form of a cyclindrical rod having essentially the same outer diameter as the catheter and a greater length than the tube, in that the mandrin is arranged to exchangeably replace the catheter when inserting the cannula in said body, and in that one end of the mandrin is arranged adjacent to the distal portion of the tube and forms a fluid-tight seal therewith in connection with said insertion.

6. The device as claimed in claim 1, wherein the sealing member is a piston-shaped member which is arranged, in a fixed or integrated manner, on the outside of the distal portion of the catheter and which has small, essentially axially directed grooves dimensioned so as not to allow fluid to pass, but to allow gas to pass.

7. The device as claimed in claim 1, wherein the catheter is made of a flexible tube material.

8. A method for injecting a substance into a body, comprising the steps of:
defining a target area,
introducing a cannula into the body so as to position a tip portion of the cannula at the target area,
delivering a determined amount of substance to the target area, and
removing the cannula,
wherein when the cannula is inserted into the body, the tip portion thereof is sealed by means of a sealing member which forms a fluid-tight seal with a surrounding tube of the cannula,
wherein the substance is injected into the target area by means of a catheter, which is surrounded by said tube and whose distal portion has, on the occasion of injection, been brought close to the distal portion of the tube,
wherein the catheter is removed from the body, thereby allowing air or gas at essentially atmospheric pressure to enter a space in the tube between the target area and the distal portion of the catheter, and
wherein the tube is removed from the body and the insertion opening for the cannula is closed.

9. The method as claimed in claim 8, wherein during said insertion, the cannula comprises a sealing mandrin of the same outer diameter as the catheter, and in that after said insertion, the mandrin is replaced by the catheter for injection.

10. The method as claimed in claim 8, wherein during said insertion, the cannula or needle member comprises the catheter which at its distal portion is provided with a piston-shaped element in sealing engagement with the surrounding tube and which is then stationary relative to the tube, and in that injection takes place through the still stationary catheter.

11. The device as claimed in claim 2, wherein a sealing member is arranged on the distal portion of the catheter in sealing engagement with the interior of the tube.

12. The device as claimed in claim 2, wherein the tube has a short distal portion having a smaller inner diameter than the remainder of the tube, and said inner diameter is essentially as large as the outer diameter of the catheter.

13. The device as claimed in claim 3, wherein the tube has a short distal portion having a smaller inner diameter than the remainder of the tube, and said inner diameter is essentially as large as the outer diameter of the catheter.

14. The device as claimed in claim 11, the tube has a short distal portion having a smaller inner diameter than the remainder of the tube, and said inner diameter is essentially as large as the outer diameter of the catheter.

15. The device as claimed in claim 2, wherein the sealing member is a piston-shaped member which is arranged, in a fixed or integrated manner, on the outside of the distal portion of the catheter and which has small, essentially axially directed grooves dimensioned so as not to allow fluid to pass, but to allow gas to pass.

16. The device as claimed in claim 3, wherein the sealing member is a piston-shaped member which is arranged, in a fixed or integrated manner, on the outside of the distal portion of the catheter and which has small, essentially axially directed grooves dimensioned so as not to allow fluid to pass, but to allow gas to pass.

17. The device as claimed in claim 4, wherein the sealing member is a piston-shaped member which is arranged, in a fixed or integrated manner, on the outside of the distal portion of the catheter and which has small, essentially axially directed grooves dimensioned so as not to allow fluid to pass, but to allow gas to pass.

18. The device as claimed in claim 11, wherein the sealing member is a piston-shaped member which is arranged, in a fixed or integrated manner, on the outside of the distal portion of the catheter and which has small, essentially axially directed grooves dimensioned so as not to allow fluid to pass, but to allow gas to pass.

19. The device as claimed in claim 2, wherein the catheter is made of a flexible tube material.

20. The device as claimed in claim 3, wherein the catheter is made of a flexible tube material.

* * * * *